United States Patent
Couston et al.

(10) Patent No.: US 8,547,542 B2
(45) Date of Patent: Oct. 1, 2013

(54) DEVICE FOR MEASURING THE FOCAL DISTANCE OF A THERMAL LENS

(75) Inventors: Laurent Couston, Villeneuve les Avignon (FR); Fabrice Canto, Boisseron (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/203,598

(22) PCT Filed: Mar. 3, 2010

(86) PCT No.: PCT/EP2010/052647
§ 371 (c)(1),
(2), (4) Date: Oct. 3, 2011

(87) PCT Pub. No.: WO2010/100168
PCT Pub. Date: Sep. 10, 2010

(65) Prior Publication Data
US 2012/0026485 A1 Feb. 2, 2012

(30) Foreign Application Priority Data
Mar. 6, 2009 (FR) ...................... 09 51426

(51) Int. Cl.
*G01B 9/00* (2006.01)
(52) U.S. Cl.
USPC ........................................................ 356/125
(58) Field of Classification Search
USPC .......................................................... 356/125
See application file for complete search history.

(56) References Cited

U.S. PATENT DOCUMENTS

| 5,561,547 A | 10/1996 | Keirstead et al. |
| 2004/0028090 A1* | 2/2004 | Pask et al. ................ 372/3 |

FOREIGN PATENT DOCUMENTS

JP         10-9811       1/1998

OTHER PUBLICATIONS

Translation of JP 10-009811 (Umemoto Masao), 1998.*
French Preliminary Search Report issued Sep. 11, 2009, French Patent Application No. FR 0951426 with English translation of category of documents.
International Search Report issued Jun. 10, 2010 in PCT/EP2010/052647.
Wayne A. Weimer, et al., "Multichannel Crossed-Beam Thermal Lens Measurements for Absolute Absorbance Determination with Pulsed Laser Excitation" Analytical Chemistry, vol. 60, No. 7, XP-002545392, Apr. 1, 1988, pp. 662-665.
D. S. Burgi, et al., "Crossed-Beam Thermal Lens Microscope", AIP Conference Proceedings USA, No. 146, XP-002545393, 1986, pp. 664-667.

(Continued)

*Primary Examiner* — Tu Nguyen
(74) *Attorney, Agent, or Firm* — Oblon, Spivak, McClelland, Maier & Neustadt, L.L.P.

(57) ABSTRACT

A method for measuring focal distance of a thermal lens located in an analyte, the method including: providing an exciting optical beam passing through the analyte and creating the thermal lens therein; emitting a coherent probe optical beam passing through the analyte and being propagated substantially perpendicular to the exciting optical beam; intercepting the probe optical beam by a detector after passing through the analyte; focusing the probe optical beam upstream or downstream of the thermal lens such that only a fraction of the probe optical beam passes through the thermal lens; acquiring an interference image by the detector; and processing the interference image to calculate the focal distance of the thermal lens. Such a method may find application in physico-chemical analysis of the analyte.

11 Claims, 6 Drawing Sheets

(56) References Cited

OTHER PUBLICATIONS

Zs Benko, et al., "Measurement of the thermal gradient in solutions generated by laser illumination", Proceedings of the SPIE—The International Society for Optical Engineering SPIE—Int. Soc. Opt. Eng USA, vol. 3407, XP-002583211, 1998, pp. 285-290.

Chenming Hu, et al., "New Thermooptical Measurement Method and a Comparison with Other Methods", Applied Optics, vol. 12, No. 1, Jan. 1973, pp. 72-79.

Thierry Berthoud, et al., "Beam Geometry Optimization in Dual-Beam Thermal Lensing Spectrometry", Analytical Chemistry, vol. 57, No. 7, Jun. 1985, pp. 1216-1219.

R. Paugstadt, et al., "Method for temporally and spatially resolved thermal-lensing measurements", Applied Optics, vol. 33, No. 6, Feb. 20, 1994, pp. 954-959.

Syun-Ru Yeh, et al., "Applications of photothermal beam deflection calorimetry to organic photochemistry", Journal of Photochemistry and Photobiology A: Chemistry, No. 87, 1995, pp. 13-21.

Raj M. Misra, et al., "Theoretical and experimental studies of pump-induced probe deflection in a thermal medium", Applied Optics, vol. 34, No. 18, Jun. 20, 1995, pp. 3358-3366.

L. Rodriguez, et al., "Fourier transforms method for measuring thermal lens induced in diluted liquid samples", Optics Communications, vol. 277, 2007, pp. 57-62.

Jerome Primot., "Three-wave lateral shearing interferometer", Applied Optics, vol. 32, No. 31, Nov. 1, 1993, pp. 6242-6249.

J. Primot, et al., "Achromatic three-wave (or more) lateral shearing interferometer", J. Opt. Soc. Am. A, vol. 12, No. 12, Dec. 1995, pp. 2679-2685.

Guy Artzner, "Aspherical wavefront measurements: Shack-Hartmann numerical and practical experiments", Pure Appl. Opt., 7, 1998, pp. 435-448.

V. V. Molebny, et al., "Refraction mapping of translucent objects with Shack-Hartmann sensor", Proc. SPIE, vol. 3548, 1998, pp. 31-33.

\* cited by examiner

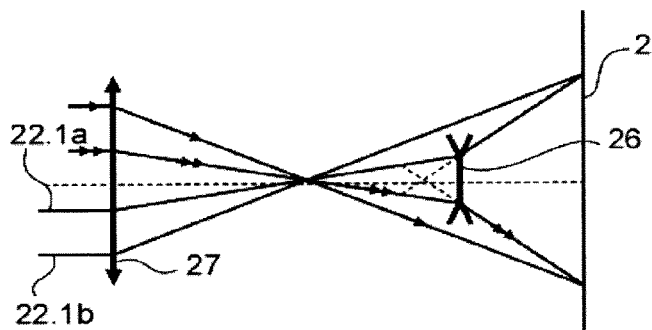
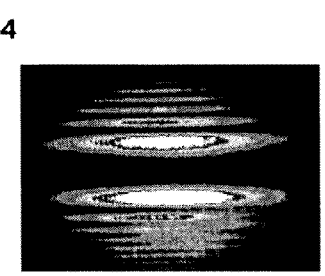
FIG. 5A
FIG. 6A
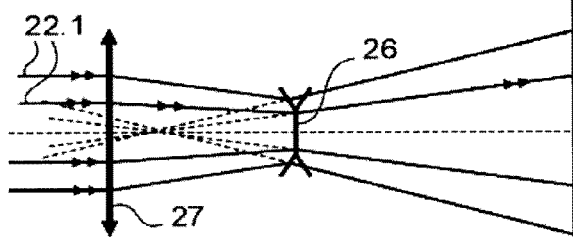
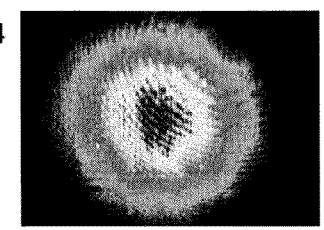
FIG. 5B
FIG. 6B
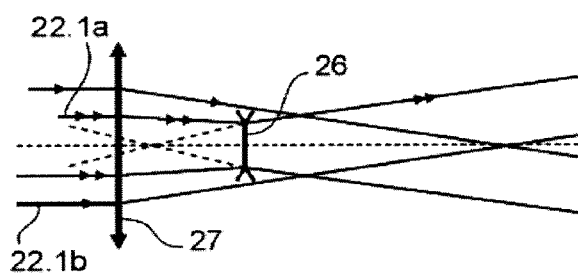
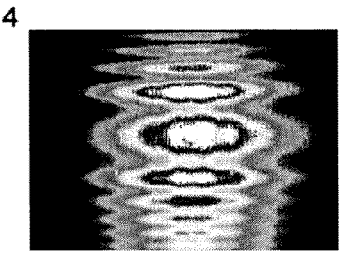
FIG. 5C
FIG. 6C

DEVICE FOR MEASURING THE FOCAL DISTANCE OF A THERMAL LENS

TECHNICAL FIELD

The present invention relates to a device for measuring the focal distance of a thermal lens created in an analyte and a device for physico-chemically analysing the analyte.

STATE OF THE PRIOR ART

Devices for measuring the focal distance of a thermal lens formed in an analyte are already known. Such a device enables in particular the analyte to be physico-chemically analysed. The principle of the formation of a thermal lens will be first reminded.

When an optical beam is absorbed by a molecule, this results in an increase in the internal energy thereof. The molecule switches to an unstable energy state, which causes it to remove the excess energy to restore its previous stable state. Several ways are then possible. It can emit an optical radiation, that is luminescence, it can emit a thermal radiation, that is vibration-rotation phenomenon, there can also be a phenomenon of energy transfer to other surrounding chemical systems.

The energy loss by the thermal way is the most frequent but there can also be a relaxation by luminescence or by energy transfer to other chemical systems.

If the energy absorbed by the analyte is significant, the sudden increase in temperature by molecular relaxation results in an expansion of the medium and thus a local decrease in the refractive index. A single virtual lens called thermal lens has been formed. The designation as thermal lens comes from the shape of the exciting optical beam, generally a laser beam, and from the energy distribution of its wave front. This thermal lens has a geometry and properties similar to those of a physical lens. The same thermal lens is not obtained depending on whether an aiming device for detecting the thermal effect and of the optical beam type is used, either in the propagation direction of the exciting optical beam or in a direction substantially perpendicular to the propagation direction.

In the first case, the thermal lens appears as a diverging spherical optical system by the combined effects of the energy gradient of the wave front of the exciting optical beam and by the angular aperture of the aiming device at the focus of the thermal lens. The thermal lens is, for a given analyte concentration, all the more divergent that the angular aperture of the aiming device is large.

In the second case, the thermal lens appears as a divergent substantially cylindrical optical system induced by the combined effects of the energy gradient deposited by the wave front of the exciting optical beam and the diameter of the exciting optical beam at the point of aim of the aiming device. The thermal lens is, for a given analyte concentration, all the more divergent that the diameter of the exciting optical beam at the point of aim is large.

It is noticed that the focal distance of the thermal lens observed with an aiming device substantially perpendicular to the propagation direction of the exciting optical beam is much lower than that of a thermal lens observed with an aiming device substantially collinear to the propagation direction of the exciting optical beam, all things being otherwise equal.

It has been shown that the focal distance of the thermal lens depends on the absorbance of the molecular species to be analysed and that this absorbance depends on the absorbing molecular species concentration as will be seen later.

From an analytical point of view, the mathematical formulation of the focal distance of the thermal lens also depends on the way of creating the thermal lens. The exciting optical beam may be or may not be focused and its emission can be pulsed or continuous. Moreover, as already set out, the aiming device which probes the thermal lens may be substantially collinear to the propagation direction of the exciting optical beam or substantially perpendicular to the latter.

FIG. 1A shows a thermal lens at which the exciting beam and the probe optical beam are substantially collinear and FIG. 1B shows a thermal lens at which the exciting optical beam and the probe optical beam are substantially perpendicular. Reference 1 corresponds to the exciting optical beam, reference 2 illustrates the probe optical beam, reference 3 illustrates the analyte, reference 4 is a filter and reference 5 is a detector. The created thermal lens is represented in dotted line and bears reference 6.

The focal distance f' of the thermal lens of FIG. 1A is given by the following expressions (1) and (2):

$$\frac{1}{f'} = \frac{2,3 \cdot \varepsilon \cdot l \cdot C \cdot P}{\pi \cdot k \cdot \omega_{OE}^2} \cdot \frac{dn}{dT} \cdot \frac{1}{1 + \frac{t_c}{2 \cdot t}} \quad (1)$$

$$\frac{1}{f'} = 8 \cdot \frac{2,3 \cdot \varepsilon \cdot l \cdot C \cdot E}{\pi \cdot \rho \cdot C_p \omega_{OE}^4} \cdot \frac{dn}{dT} \cdot \frac{1}{\left(1 + \frac{t}{2 \cdot t_c}\right)^2} \quad (2)$$

with:
$t_c$ lifetime of the thermal lens such that:

$$t_c = \frac{\omega_{OE}^2 \cdot \rho \cdot C_p}{4 \cdot k}$$

k thermal conductivity of the analyte in $W \cdot cm^{-1} \cdot K^{-1}$,
$\rho$ density of the analyte in $g \cdot cm^{-3}$,
$C_p$ heat capacity of the analyte in $J \cdot g^{-1} \cdot K^{-1}$,
$\omega_{OE}$ radius of the exciting optical beam at the analyte in cm,
$\varepsilon$ molar absorption coefficient of the analyte (also called molar extinction coefficient), representing the capacity of an element to absorb light, expressed in $dm^3 \cdot cm^{-1} \cdot mol^{-1}$,
C analyte concentration in $mol \cdot dm^{-3}$,
l length of the optical path in the analyte in cm,
E energy of the pulsed exciting laser in J,
P power of the continuous exciting laser in W, $$\frac{dn}{dT}$$

refractive index gradient of the analyte in $K^{-1}$.

Expression (1) corresponds to the case where exciting optical beam 1 is continuous and expression (2) corresponds to the case where the exciting optical beam 1 is pulsed.

In FIG. 1B, the probe optical beam 2 is focused in the vicinity of the thermal lens 6. Such a configuration enables analytes with very small volumes in the order of a few picoliters to be used, if they are liquid or gaseous analytes or of a few $10^{-12}$ cubic decimeters. However, it is worthy of note that the experimental implementation is quite delicate.

The focal distance f' of the thermal lens of FIG. 1B is given by the following expressions (3) and (4):

$$\frac{1}{f'} = \frac{2,3 \cdot \varepsilon \cdot C \cdot P}{\sqrt{2 \cdot \pi} \cdot k \cdot \omega_{OE}} \cdot \frac{dn}{dT} \cdot \left[1 - \frac{1}{\left(1 + \frac{2t}{t_c}\right)^{1/2}}\right] \quad (3)$$

$$\frac{1}{f'} = \frac{2^{5/2}}{\sqrt{\pi}} \cdot \frac{2,3 \cdot \varepsilon \cdot C \cdot E}{\rho \cdot C_p \cdot \omega_{OE}^3} \cdot \frac{dn}{dT} \cdot \frac{1}{\left(1 + \frac{2 \cdot t}{t_c}\right)^{3/2}} \quad (4)$$

Expression (3) corresponds to the case where the exciting optical beam 1 is continuous and the expression (4) corresponds to the case where the exciting optical beam 1 is pulsed.

If the exciting optical beam 1 is continuous, it is preferable to use a mechanical shutter between the optical source generating the exciting optical beam (not represented) and the analyte to enable the analyte to be thermally relaxed. A continuous exciting optical beam 1, coupled to a mechanical shutter, provides numerous excitation modes enabling to vary the excitation time of the analyte and the duty cycle between the excitation of the analyte and the absence of excitation. It will be noted that the analyte should be excited for a time to achieve a steady state.

Several methods are known for measuring the focal distance of a thermal lens and inferring therefrom, for example, a molecular species concentration in an analyte.

In FIGS. 2A, 2B and 2C a device for measuring a focal distance of a known thermal lens 3 is represented. Such a device is for example described in documents [1], [2] referred to at the end of the present description. The probe optical beam 2 passes through a diaphragm 7 before being intercepted by the detector 5 which is of the photodiode type. The exciting optical beam is not represented. The diaphragm 7 lies between the analyte 3 and the detector 5. The detector may or may not be associated with a dioptrics optical system (not represented). The ratio of intensities acquired by the detector 5 is measured in two configurations: in the first configuration, illustrated in FIG. 2A, the thermal lens is not created, namely the exciting optical beam does not illuminate the analyte. In the second configuration, the thermal lens 6 is present.

FIG. 2C is to be considered together with FIG. 2A. The intensity acquired by the detector 5 is measured in the configuration illustrated in FIG. 2A. In a second configuration, the thermal lens 6 is present, and the detector 5 or the detector-dioptrics optical system assembly, if any, is moved in the propagation direction of the probe optical beam until the intensity acquired by the detector 5 is equal to that measured in the first configuration. Knowing the distance Δz, corresponding to the displacement of the detector 5 enables to deduce the focal distance of the thermal lens 6.

In FIG. 2D, another device for measuring the focal distance of a known thermal lens 6 is illustrated. Such a device is for example described in documents [3], [4], [5] referred to at the end of the present description. The intensity acquired by the detector 5 is measured in the configuration illustrated in FIG. 2A. Once the thermal lens 6 is created, the probe optical beam 2' is deflected with respect to the propagation direction of the probe optical beam upstream of the analyte 3. By measuring the deviation Δx which enables to obtain the same intensity, the focal distance can be deduced.

There are also methods for calculating the focal distance of a thermal lens which use interferences. In FIG. 3A, a Fizeau interferometer is represented. Such a device is for example described in document [6] referred to at the end of the present description. Two probe optical beams 2.1, 2.2 coming from the same optical source are used. The probe optical beam 2 is split in two by passing through a beam splitter 8 located upstream of the analyte 3. One of the probe optical beams 2.1 passes through the analyte 3 in an area free of thermal lens and the other probe optical beam 2.2 passes through the analyte at an area containing the thermal lens 6. Both optical beams which leave the analyte 3 have the reference numbers 2.1' and 2.2'. The thermal lens 6 causes a phase shift between both optical beams 2.1' and 2.2' leaving the analyte 3 and interferences occur. The detector 5 intercepts both optical beams and reveals an interference figure. This interference figure enables to deduce the source wave front and the focal distance of the thermal lens.

In FIG. 3B, a Michelson interferometer is represented. Two identical analytes 3.3' are used. In one, bearing reference number 3, a thermal lens 6 is formed, and the other bearing reference number 3' is free of thermal lens. The probe optical beam 2 arrives in a beam splitter 9. The beam splitter 9 deviates a first part of the probe optical beam 2.3 to the first analyte 3, this first part of the probe optical beam 2.3 passes through the first analyte 3 a first time, it is reflected on a mirror 10.1 and passes through the first analyte 3 a second time, it passes through the beam splitter 9 and reaches a detector 5. The beam splitter 9 allows a second part of the probe optical beam 2.4 to pass through the second analyte 3'. The second part of the probe optical beam 2.4 passes through the second analyte 3', is reflected by a second mirror 10.2, passes again through the second analyte 3' and is reflected by the beam splitter to the detector 5. There is a path difference between both parts of the probe optical beam 2.3, 2.4 because of the presence of the thermal lens 6 in the first analyte 3.

In FIG. 3C, there is another interferometric device represented with a beam splitter 9, and two mirrors 10.1, 10.2 enabling to disturb the interference figure of the wave front by the thermal lens and to deduce physical characteristics therefrom. Such a device is for example described in documents [7], [8] referred to at the end of the present description. In this case, there is only one analyte 3 wherein the thermal lens 6 is formed. The probe optical beam 2 passes through the thermal lens 6 before being separated into two parts 2.5, 2.6 which will have optical paths with difference lengths, because one of the mirrors 10.2 is farther from the beam splitter 9 than the other. The optical path of the optical beam 2.6 is longer than that of the optical beam 2.5. The thermal lens 6 distorts the wave front of the probe optical beam 2 before it is separated. The interferences obtained on the detector 5 will reflect the appearance of the thermal lens and its focal distance.

In FIGS. 3D1, 3D2 a Shack-Hartmann analyser is represented. Such a device is described for example in documents [9], [10] referred to at the end of the present description. This apparatus includes an array of microlenses 12 placed in front of a detector 5. The probe optical beam 2 first passes through the analyte 3 to be analysed, then through the array of microlenses 12 before it is intercepted by the detector 5. The geographical lighting difference intercepted by the detector 5 is measured in two configurations: in the first configuration, illustrated in FIG. 3D1, the thermal lens is not created, namely the exciting optical beam (not represented) does not illuminate the analyte 3. In the second configuration illustrated in FIG. 3D2, the thermal lens 6 is present in the analyte 3. Thus, depending on the appearance of the wave front of the optical beam emerging from the analyte 3 and passing through the array of microlenses 12, different deviations will occur. The wave fronts bear reference number 13.

The lighting intercepted by the detector 5 in both configurations corresponds to a primary distortion of the wave front by an interference-free single convolution. It is possible to deduce the lens geometry from the obtained lightings.

In the above described devices, only those which carry out intensity measurements are used for concentration measurement purposes. The concentration measurements pose the problem of the stability in the lighting intensity of the source and its possible absorption by the medium investigated.

The measurements performed can not be reliable because of the instability causing fluctuations in the intensity of laser sources, the instability in the transmission of the probe optical beam when the analyte absorbs the probe optical beam, and the mechanical instability inherent to the extremely accurate optical adjustments of the optical sources for the intersection between the exciting optical beam and the probe optical beam to be located at their optical axes. Controlling this intersection at the micron scale is difficult because it depends on thermal variations, mechanical impacts and slight variations in the analyte refractive index, caused by a slight variation in temperature, or in the chemical composition of the analyte called "matrix effect" in the analysis field. More precisely, the matrix effect corresponds to the influence of the chemical environment on the analyte atoms.

These disturbances condemn these measurement techniques because they have low reproducibility levels, only 30% according to some authors. These techniques are often incompatible with the constraints of the physico-chemical analysis. Another drawback of the devices which have moving parts such as those illustrated in FIGS. 2A, 2C and 2D is that they are often not robust enough.

The interference or Shack-Hartman devices are intended to investigate the thermal lens geometries.

Configurations which use interferences involve processes which require the implementation of two measurement ways. Calibrating the device is complicated because of the local observation of the spatial interference and of a strongly altered wave front upon passing through the thermal lens.

Finally, the Shack-Hartmann analyser is a device with a low sensitivity and difficult to transpose to the quantitative measurement of chemical species.

DESCRIPTION OF THE INVENTION

One object of the present invention is actually to provide a method for measuring the focal distance of a thermal lens created in an analyte which does not have the above-mentioned drawbacks and in particular, which is not sensitive to energy variations of the source generating the probe optical beam.

Another object of the invention is to provide such a method which does not depend on energy variations transmitted by the source generating the probe optical beam under the influence of its absorption by the analyte.

Still another object of the invention is to provide such a method which does not depend on slight geometrical variations at the intersection between the probe optical beam and the exciting optical beam.

A method for measuring the focal distance of a thermal lens created in an analyte according to the invention includes the steps of:

providing an exciting optical beam by an exciting optical source, such exciting optical beam passing through the analyte and creating the thermal lens therein, such thermal lens being unique and of substantially cylindrical geometry, emitting a coherent probe optical beam by a probe optical source, such probe optical beam passing through the analyte and being propagating substantially perpendicular to the exciting optical beam, intercepting the probe optical beam by a detector after its passing through the analyte, characterised in that it further includes the steps of focusing the probe optical beam upstream or downstream of the thermal lens such that only a fraction of the probe optical beam passes through the thermal lens, acquiring an interference image by the detector, processing the interference image for calculating the focal distance of the thermal lens.

Advantageously, the exciting optical beam is a laser beam.

The method may further include a step of focusing the exciting optical beam before it passes through the analyte by focusing means, which enables an analyte with a small size to be used.

The detector may be a CCD camera.

It is preferable that the method includes a step for triggering the detector in synchronism with the exciting optical source to guard against the electrical field noise of the pulse of the probe optical beam and against Rayleigh and Raman scatterings.

The exciting optical source may be pulsed or continuous.

There is preferably provided a step of setting the intensity of the probe optical beam by setting means located upstream of the analyte, wherein the setting means may be a rotary filter having a variable, increasing or decreasing absorbance.

The present invention also relates to a method for physico-chemically analysing an analyte, including the steps of the method for measuring the focal distance thus characterised in a step for determining at least a physico-chemical magnitude relating to the analyte using determining means, this magnitude depending on the measured focal distance.

The physico-chemical magnitude may be the analyte concentration, absorbance, heat capacity, thermal conductivity, density or molar absorption coefficient.

The present invention also relates to a device for measuring the focal distance of a thermal lens created in an analyte including an exciting optical source for providing an exciting optical beam passing through the analyte and creating therein the thermal lens, a probe optical source for emitting a coherent probe optical beam passing through the analyte and being propagated substantially perpendicular to the exciting optical beam, a detector for intercepting the probe optical beam after passing through the analyte. The measuring device further includes means for focusing the probe optical beam upstream or downstream of the thermal lens such that only a fraction of the probe optical beam passes through the thermal lens and an interference image is acquired by the detector, means for processing the interference image to calculate the focal distance of the thermal lens.

BRIEF DESCRIPTION OF THE DRAWINGS

The present invention will be better understood upon reading the description of exemplary embodiments given by way of purely indicative and not in the least limiting example, referring to the appended drawings in which:

FIGS. 3D1 and 3D2 already described, show a device for measuring the focal distance of a thermal lens created in a Shack-Hartmann type analyte;

FIGS. 5A and 5C respectively show the means for focusing the probe optical beam of the measuring device of FIG. 4, in a configuration wherein focusing is made on the one hand upstream of the thermal lens and on the other hand downstream of the thermal lens, FIG. 5B shows a configuration excluded at the thermal lens;

FIGS. 6A, 6B and 6C show the alteration of the wave front of the probe optical beam intercepted by the detector in the three configurations of FIGS. 5A, 5B and 5C;

Identical, similar or equivalent parts of the different figures described hereinafter bear the same reference numbers so as to make it easier to pass from one figure to another.

Different parts represented on figures are not necessarily drawn using the same scale, to make figures intelligible.

DETAILED DESCRIPTION OF PARTICULE EMBODIMENTS

Figure 1A:
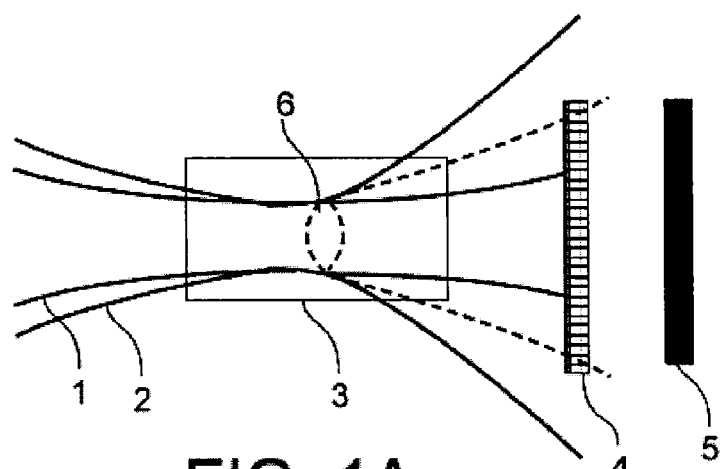
FIGS. 1A and 1B, already described, show both types of thermal lens created in an analyte.
Figure 1B:
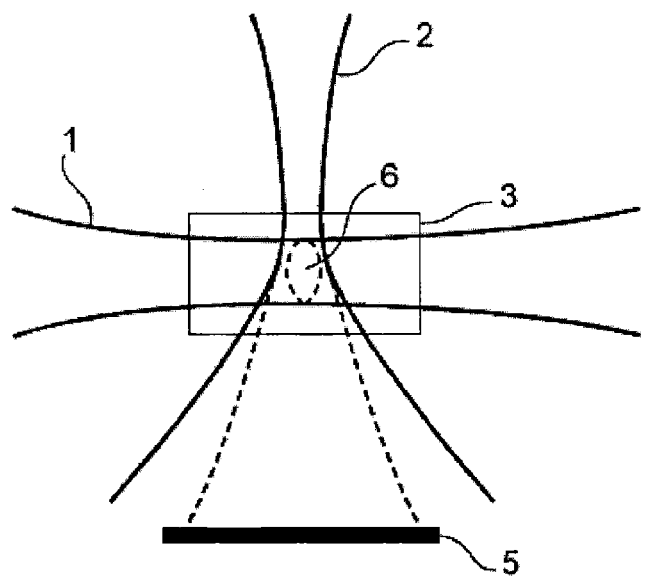
Figure 2A:
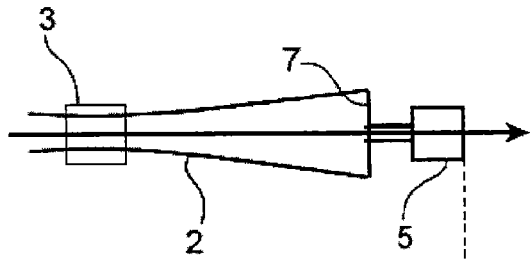
FIGS. 2A, 2B, 2C and 2D, already described, show devices for measuring the focal distance of a thermal lens created in an analyte, of known types, with movable parts.
Figure 2B:
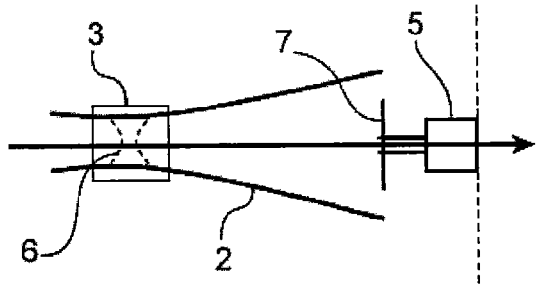
Figure 2C:
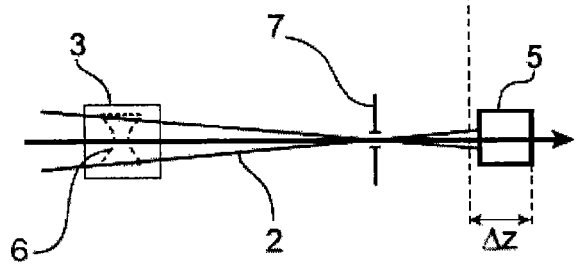
Figure 2D:
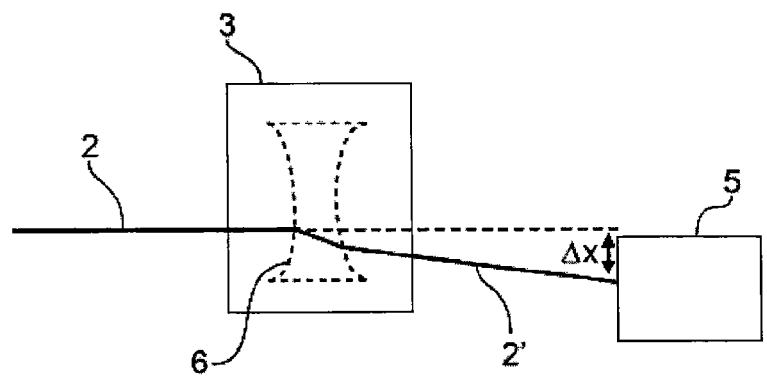
Figure 3A:
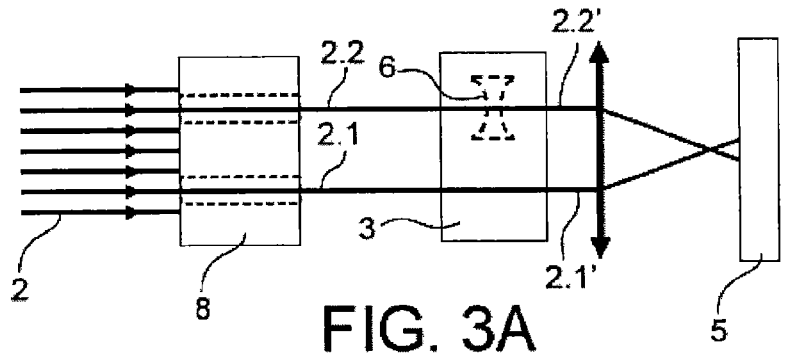
FIGS. 3A, 3B and 3C already described, show devices for measuring the focal distance of a thermal lens created in an analyte, of known types, operating with interferences.
Figure 3B:
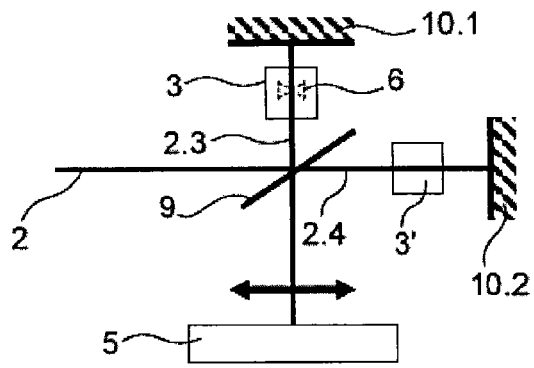
Figure 3C:
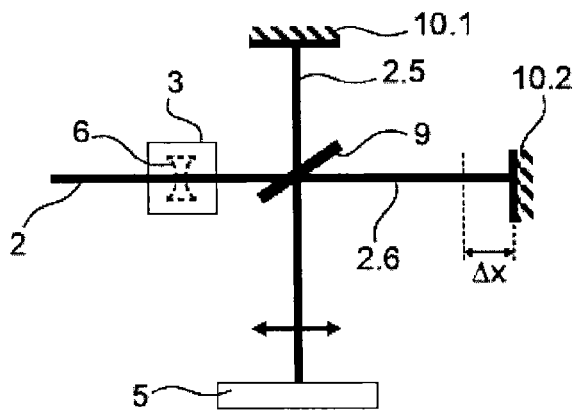
Figure 4:
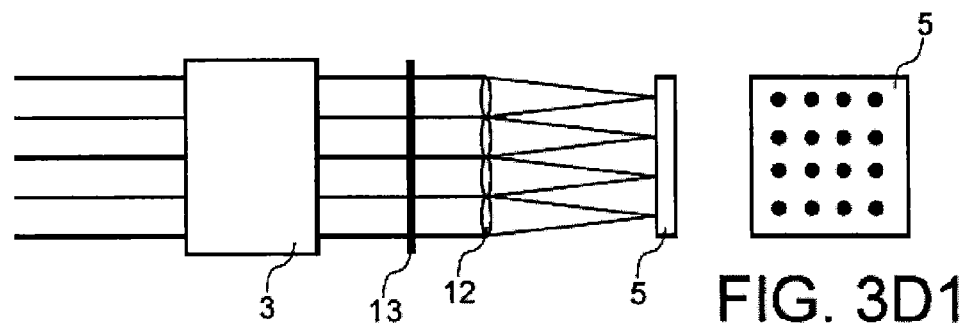
FIG. 4 shows a device for measuring the focal distance of a thermal lens created in an analyte according to the invention as well as a device for physico-chemically analysing an analyte being an object of the invention, these devices allowing the implementation of the methods according to the invention.
Figure 4:
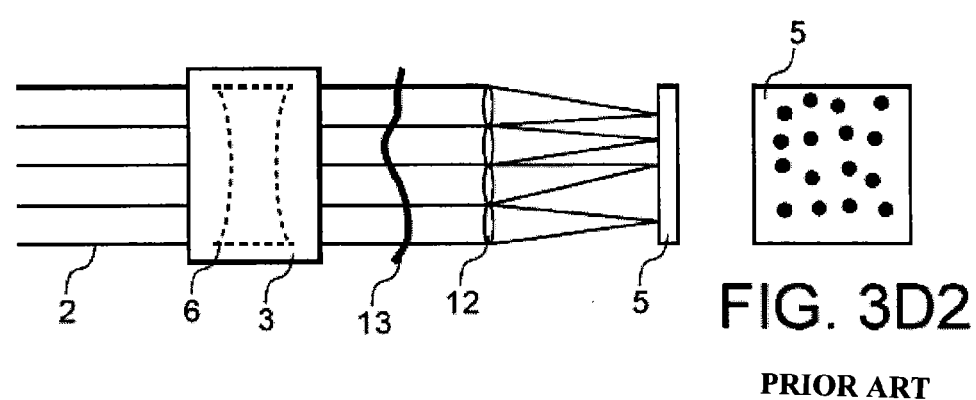
Figure 4:
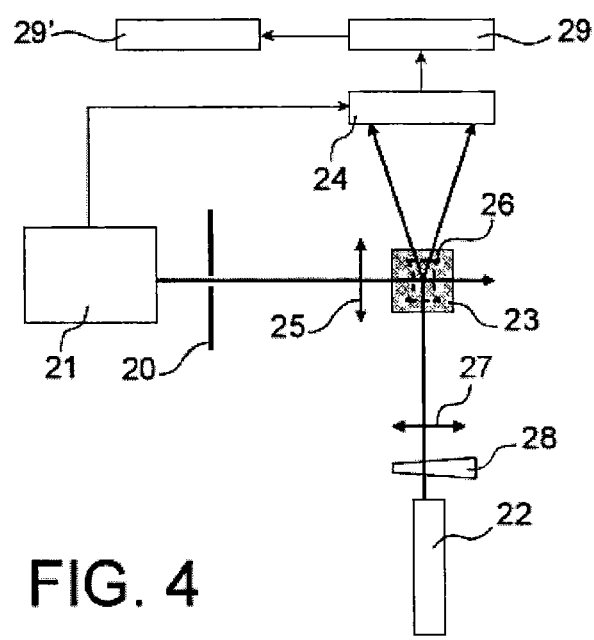

FIG. 4 will now be referred to. It schematically shows a device for measuring the focal distance of a thermal lens 26 created in an analyte 23. In this invention, it is understood that the analyte is a single phase medium wherein one or more chemical species are dissolved. The analyte 23 can be liquid, gaseous or solid.

This measuring device allows the implementation of the method according to the invention.

It includes an exciting optical source 21 for emitting an exciting optical beam 21.1 which passes through the analyte 23 and creates the thermal lens 26 therein. This thermal lens is unique and of a substantially cylindrical geometry as discussed above. The exciting optical source 21 is a laser source which has a wavelength adjusted with the absorption wavelength of a chemical species of the analyte, the latter contributing to create the thermal lens. For example in the case of an analyte formed of an ethanol and cobalt solution, the wavelength of the exciting optical source will be about 532 nm. The exciting optical source 21 could be continuous or pulsed. A mechanical shutter 20 is provided between the exciting optical source 21 and the analyte 23 if the exciting optical source 21 is continuous.

The measuring device, object of the invention, also includes a probe optical source 22 for emitting a probe optical beam 22.1. The probe optical beam 22.1 is used to detect the thermal effect created by the exciting optical beam 21.1. The probe optical beam 22.1 is propagated towards the analyte 23 and passes through it. The propagation direction of the probe optical beam 22.1 is substantially perpendicular to that of the exciting optical beam. The probe optical beam 22.1 is a coherent optical beam, preferably monochromatic. It is preferably a continuous optical beam, but it could be pulsed. The probe optical beam 22 can be a HeNe laser source the wavelength of which is about 633 nm and the energy of which may be adjusted, while of course preserving coherence. After passing through the analyte 23, the probe optical beam 22.1 is intercepted by a detector 24 for measuring the intensity of the wave front of the probe optical beam (invisible in FIG. 4). It can be a CCD (charge coupled device) type camera.

The measuring device according to the invention further includes means 27 for focusing the probe optical beam 22.1, focusing being made upstream or downstream of the thermal lens 26 but not at the thermal lens. Moreover, focusing is such that only a fraction of the probe optical beam 22.1 passes through the thermal lens 26. Details will be given subsequently. The focusing means 27 are placed between the probe optical source 22 and the analyte 23. FIGS. 5A and 5C which illustrate this can be referred to. It is assumed in the described example that the means 27 for focusing the probe optical beam 22 have a focal distance of about 100 mm. Of course, this is only a non-limiting example, and this focal distance value may be different depending on the size of the detector 24 and on the expected sensitivity.

It is possible for the measuring device being an object of the invention to further include means 25 for focusing the exciting optical beam. They are placed between the exciting optical source 21 and the analyte 23. They enable an analyte 23 with a small size to be used. In the described example, the focal distance of the means for focusing the exciting optical beam 21.1 can be of about 25.4 mm. This focal distance value can be different depending on the expected sensitivity of the measuring device.

The measuring device according to the invention can further include a filter 28 for adjusting the intensity of the probe optical beam 22. The filter is placed between the probe optical source 22 and the means 27 for focusing the probe optical beam. The filter 28 may be of the rotary type with increasing or decreasing absorbance.

The detector 24 delivers a signal which is injected in processing means 29 for calculating the focal distance of the thermal lens 26.

It is assumed that in FIG. 4, the device represented is a device for physico-chemically analysing an analyte. It includes, in addition to the measuring device, determining means 29' for determining at least a physico-chemical magnitude relating to the analyte 23, this magnitude depending on the focal distance. These determining means 29' receive the focal distance calculated by the processing means 29 and deliver at least one physico-chemical magnitude relating to the analyte 23. Of course, this magnitude depends on the calculated focal distance. It can be, for example, the analyte concentration, that is the concentration of a chemical species contained in the analyte, absorbance, heat capacity, thermal conductivity, density or molar absorption coefficient thereof.

The determining means 29' can be mistaken with the processing means 29.

It is preferable for the detector 24 to be triggered in synchronism with the exciting optical source 21 so as to guard against electrical field noise of the laser beam and Rayleigh and Raman scatterings of the analyte 23.

FIG. 5A illustrates the case where the means 27 for focusing the probe optical beam 22.1 are focused upstream of the thermal lens 26. FIG. 5C illustrates the case where the means 27 for focusing the probe optical beam 22.1 are focused downstream of the thermal lens 26. In both cases, only a fraction 22.1a of the probe optical beam 22.1 passes through the thermal lens 26. The complementary fraction of the probe optical beam 22 which does not pass through the thermal lens 26, bears reference number 22.1b. Both fractions 22.1a and 22.1b of the probe optical beam 22 will form an interference image on the detector 24. On the detector 24 waves which have not travelled the same optical path are combined. As a result, there are alternating constructive waves and destructive waves the fringe spacing of which depends on the focal distance of the thermal lens 26.

In FIG. 5B, the probe optical beam 22.1 is focused on the thermal lens 26. All the rays from this optical beam 22.1 pass through the thermal lens 26 and there is no interference at the detector 24. The configuration of FIG. 5B is not part of the invention.

In FIGS. 6A, 6B and 6C an image delivered by the detector 24 is represented whereas the means for focusing the probe optical beam correspond to those of FIGS. 5A, 5B and 5C, respectively. FIGS. 6A and 6C are exploitable interference images. In FIG. 6B, there is no interference and this image is not exploitable.

In order to decrease the bulk of the measuring device object of the invention, it is preferable to choose the configuration of FIG. 5C wherein the focuses and the spatial adjustments are such that the thermal lens 26 is located above the focusing point of the probe optical beam. For the same purpose, it is important to ensure that the thermal lens has a cross-section area lower than that of the probe optical beam.

Figure 7:
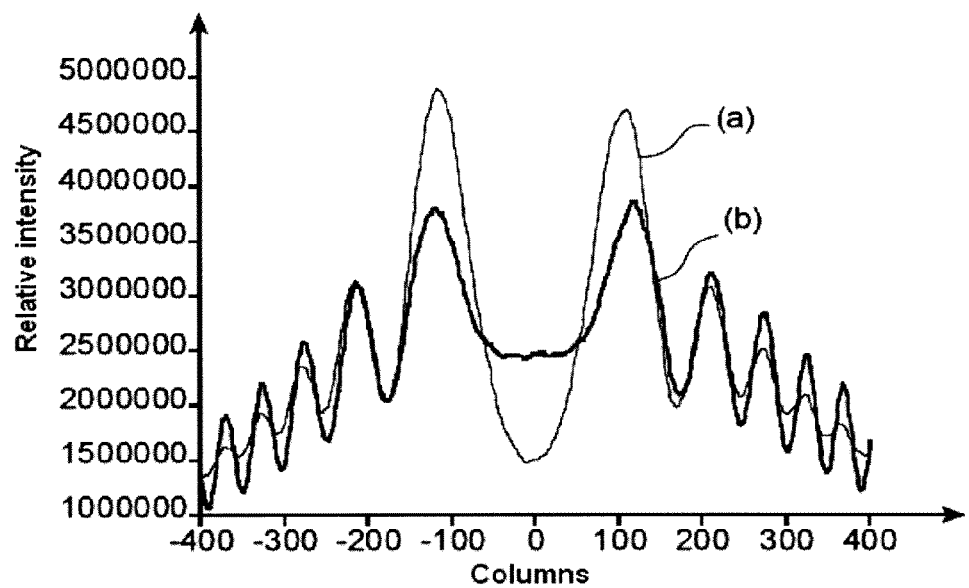
FIG. 7 shows an interferogramme obtained with the device of FIG. 4 and a theoretical interferogramme obtained under the same conditions.

FIG. 7 illustrates with reference (a) an interferogramme obtained from the interference image acquired by the detector illustrated in FIG. 6A. For this, the processing means added, row by row, the intensities acquired by each pixel of the row. The interferogramme bearing the reference (b) is a theoretical interferogramme corresponding to the same conditions.

The following simplified hypotheses are applied. The Gauss conditions are met. The thermal lens created is of substantially cylindrical geometry. The effects of the thermal lens are prevailing in the phase shift of waves which reach the detector. The thickness of the thermal lens is neglected.

In this interferogramme, the intensity I(x) at the dimension x can be expressed according to the usual formula of the amplitude division Michelson interferometer:

$$I(x) = 2I_x (1 + \cos(\Delta\varphi_x)) \quad (6)$$

$$\text{with } \Delta\varphi = \frac{2 \cdot \pi \cdot \delta_x}{\lambda} \quad (6')$$

$I_x$ is the intensity of the probe optical beam at the dimension x in the absence of thermal lens, $\lambda$ is the wavelength of the probe optical beam, $\delta_x$ the path difference between both fractions of the probe optical beam.

Let us set:

D the distance between the thermal lens and the detector

L the distance between the means for focusing the probe optical beam and the thermal lens $f'_{LT}$ the focal distance of the thermal lens $f'_{LF}$ the focal distance of the means for focusing the probe optical beam Then $$\delta_x = \frac{D \cdot x^2}{2} \cdot \left[ \frac{1}{(D - f'_{LF} + L)^2} - \frac{1}{\left( \left| \frac{f'_{LT}(f'_{LF} - L)}{f'_{LF} - L + f'_{LT}} \right| + D \right)^2} \right] \quad (7)$$

By introducing the path difference induced by the means for focusing the probe optical beam to meet the boundary conditions, the final expression of the intensity I(x) at the dimension x becomes:

$$I(x) = I_x + \frac{I_x}{2} \cdot \cos(\varphi_{cste} - \Delta\varphi_x) \quad (8)$$

with $$\varphi_{cste} = D \cdot x^2 \cdot \left[ \frac{1}{(D - f'_{LF} + L)^2} - \frac{1}{D^2} \right] \quad (9)$$

It is supposed that in the measuring device according to the invention used in this series of measurements and implementing the measuring method according to the invention:

D=132 mm

L=128 mm $f'_{LF}$=100 mm, the focal distance $f'_{LT}$ of the thermal lens is optimised by the least square method to fit the theoretical function to the experimental interferogramme shown in FIG. 7. Of course, these values may vary depending on the analytes. For an analyte that is a cobalt-containing ethanol solution and for which the cobalt concentration is 0.1 mol/L, the theoretical focal distance $f'_{LT}$ of the thermal lens is −10.4 mm.

The focal distance $f'_{LT}$ calculated by the processing means is −10.4 mm.

Figure 8:
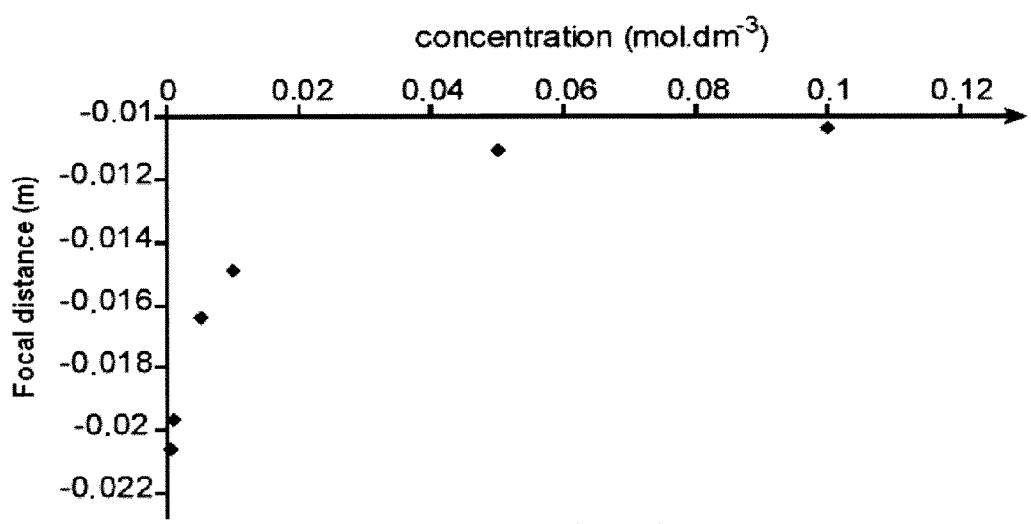
FIG. 8 shows the variation in the focal distance of a thermal lens created in an ethanol and cobalt solution as a function of the cobalt concentration, this focal distance being measured by the measuring device object of the invention by implementing the method of the invention.

Let us now turn to FIG. 8 which shows a calibration curve expressing the focal distance of a thermal lens produced in an analyte which is an ethanol and cobalt solution as a function of the cobalt concentration.

The ethanol and cobalt solution has the following characteristics:

Molar absorption coefficient: $\epsilon$=20 dm$^3$·mol$^{-1}$ cm$^{-1}$.

Thermal conductivity: k=0.0018 W·cm$^{-1}$·K$^{-1}$

Density: $\rho$=0.789 g·cm$^{-3}$

Heat capacity: $C_p$=2.44 J·g$^{-1}$·K$^{-1}$

Refractive index gradient: dn/dT=397.10$^{-6}$ K$^{-1}$.

It has been investigated through TLS (thermal lens spectroscopy) on concentrations ranging from 5.10$^{-4}$ to 0.1 mol/L.

The exciting optical beam is pulsed and its wavelength is equal to 532 nm. The wavelength of the probe optical beam is 633 nm. The probe optical beam is continuous.

The analyte is introduced into a quartz vessel with an optical path length of 1 mm, without stirring. Other containers with different dimensions can of course be used.

For each concentration, an interferogramme is measured by the measuring device object of the invention, upon implementing the measuring method according to the invention and the focal distance is inferred using equation [8].

The appearance of the curve of FIG. 8 corresponds to the one expected by equation [8] to a nearest factor introduced because there is no analyte turnover after each pulse of the exciting optical beam.

The measurement sensitivity is equivalent to that obtained through molecular absorption spectrophotometry whereas the probed volumes may be lower by several orders of magnitude. The usual performances in the thermal lens spectrometry are not altered.

One advantage of the measuring device according to the invention and the corresponding method is that the interference image acquired by the detector is independent of the intensity of the probe optical beam or its possible absorption by the analyte. The filter can absorb part of the probe optical beam, but its role is to optimise the intensity arriving on the detector so that it does not saturate.

Another point of this measuring device and the corresponding method is that the signal delivered by the detector is not very dependent on the mechanical conditions for adjusting different optical components between each other.

The measuring device being an object of the invention and the corresponding method enable the analysis techniques using a thermal lens to be substantially improved.

The points of the improvement are the following.

The measurement is independent with respect to the intensity of the wavelength received by the detector. The concrete aspects of this improvement are as follows, it is not required to control the probe optical source in energy, that the probe optical source does not need to be stabilised in energy, and that the analyte can be absorbing at the wavelength of the probe optical beam.

The setting stability is much better than in prior art, this because of less constrained mechanical adjustments of components of the measuring device.

The interferogramme induced by the thermal lens can be exploited in an analytical approach.

DOCUMENTS QUOTED

[1] « New thermooptical measurement method and a comparison with other methods », Chenming hu and J. R Whinnery, Applied optics, vol 12, No 1, pages 72-79 (1973);

[2] « Beam geometry optimization in dual-beam thermal lensing spectrometry », T. Berthoud, N. Delorme and P. Mauchien Anal. Chemistry, vol 57, No 7, pages 1216-1219 (1985);

[3] « Method for temporally and spatially resoved thermal-lensing measurements », R. Paugstadt and M. Bass, Applied optics, vol 33, No 6, pages 954-959 (1994);

[4] « Applications of photothermal beam deflection calorimetry to organic photochemistry », Syun-Ru and Daniel E. Falvey, Journal of photochemistry and photobiology, A: chemistry, No 87, pages 13-21 (1995);

[5] « Theoretical and experimental studies of pump-induced probe deflection in a thermal medium », Raj M. Misra and Partha P. Banerjee, Applied optics, vol 34, No 18, pages 3358-3366 (1995);

[6] « Fourier transforms method for measuring thermal lens induced in diluted liquid samples », L. Rodriguez and R. Escalonia, Optics communications, No 227, pages 57-62 (2007);

[7] « Three waves lateral shearing interferometer », J. Primot, Applied optics, vol 32, No 31, pages 6242-6249 (1993);

[8] « Achromatic three waves (or more) lateral shearing interferometer », J. Primot et L. Sogno, Optical society of America, vol 12, No 12, pages 2679-2685 (1995);

[9] « Aspherical wavefront measurements: Shack-Hartmann numerical and practical experiments », G. Artzner, Pure Applied Opt. 7, pages 435-448 (1998);

[10] « Refraction mapping of translucent objects with Shack-Hartmann sensor » V. V. Molebny, R. Gordon, V. N. Kurashov, D. V. Podanchuk, V. Kovalenko et J. Wu, Proc. SPIE, No 3548, pages 31-33 (1998).

The invention claimed is:

1. A method for measuring focal distance of a thermal lens created in an analyte comprising:
    providing an exciting optical beam by an exciting optical source, such exciting optical beam passing through the analyte and creating the thermal lens, such thermal lens being virtual, unique and of substantially cylindrical geometry;
    emitting a coherent probe optical beam by a probe optical source, such probe optical beam passing through the analyte and being propagated substantially perpendicular to the exciting optical beam;
    intercepting the probe optical beam by a detector after passing through the analyte;
    focusing the probe optical beam upstream or downstream of the thermal lens such that only a fraction of the probe optical beam passes through the thermal lens;
    acquiring an interference image by the detector; and
    processing the interference image to calculate the focal distance of the thermal lens.

2. The measuring method according to claim 1, wherein the exciting optical beam is a laser beam.

3. The measuring method according to claim 1, further comprising focusing the exciting optical beam before passing through the analyte by focusing means.

4. The measuring method according to claim 1, wherein the detector includes a CCD camera.

5. The measuring method according to claim 1, further comprising triggering the detector in synchronism with the exciting optical source.

6. The measuring method according to claim 1, wherein the exciting optical source is pulsed or continuous.

7. The measuring method according to claim 1, further comprising setting intensity of the probe optical beam by setting means located upstream of the analyte.

8. The measuring method according to claim 7, wherein the setting means includes a rotary filter having a varying, increasing, or decreasing absorbance.

9. A method for physico-chemically analysing an analyte comprising:
    the method for measuring the focal distance according to claim 1; and
    determining at least one physico-chemical magnitude relating to the analyte through determining means, the magnitude depending on the measured focal distance.

10. Analysing method according to claim 9, wherein the physico-chemical magnitude is the analyte concentration, absorbance, heat capacity, thermal conductivity, density, or molar absorption coefficient.

11. A device for measuring focal distance of a thermal lens created in an analyte comprising:
    an exciting optical source for providing an exciting optical beam which passes through the analyte and creates therein the thermal lens which is virtual, unique, and substantially cylindrical;
    a probe optical source for emitting a coherent probe optical beam which passes through the analyte and is propagated substantially perpendicular to the exciting optical beam;
    a detector for intercepting the probe optical beam after passing through the analyte;
    means for focusing the probe optical beam upstream or downstream of the thermal lens such that only a fraction of the probe optical beam passes through the thermal lens and an interference image is acquired by the detector; and
    means for processing the interference image to calculate the focal distance of the thermal lens.

* * * * *